United States Patent
Hayashi

(10) Patent No.: US 10,946,552 B2
(45) Date of Patent: Mar. 16, 2021

(54) EVALUATION METHOD FOR CLAY AND MANUFACTURING METHOD OF EXTRUSION MOLDED BODY

(71) Applicant: DENSO CORPORATION, Kariya (JP)

(72) Inventor: Naohiro Hayashi, Kariya (JP)

(73) Assignee: DENSO CORPORATION, Kariya (JP)

( * ) Notice: Subject to any disclaimer, the term of this patent is extended or adjusted under 35 U.S.C. 154(b) by 480 days.

(21) Appl. No.: 15/946,913

(22) Filed: Apr. 6, 2018

(65) Prior Publication Data

US 2018/0304494 A1 Oct. 25, 2018

(30) Foreign Application Priority Data

Apr. 19, 2017 (JP) ............... JP2017-082908

(51) Int. Cl.
  *B28C 1/16* (2006.01)
  *B28C 5/42* (2006.01)
  (Continued)

(52) U.S. Cl.
  CPC ........ *B28C 5/4258* (2013.01); *B01D 46/2474* (2013.01); *B28B 17/0072* (2013.01);
  (Continued)

(58) Field of Classification Search
  CPC ....... B28C 5/4258; B28C 5/4286; B28C 1/16; B28C 1/227; B28C 7/02; B28B 17/0072; B28B 17/0081; B28B 3/22; B28B 3/269; B29C 48/0015; B29C 48/11; B29C 48/32; B29C 48/385; B29C 48/362; B29L 2031/608; B01D 46/2474; B01D 2046/2496; C04B 38/0006; C04B 38/0009; C04B 35/195; C04B 35/62635; C04B 35/6263; C04B 2235/6021; C04B 2235/349; C04B 2111/0081; C04B 2111/40; F01N 3/035; F01N 3/0222;
  (Continued)

(56) References Cited

U.S. PATENT DOCUMENTS

| 2003/0098530 | A1 | 5/2003 | Inoguchi |
| 2010/0102491 | A1* | 4/2010 | Inoguchi ................. C04B 35/63 264/630 |
| 2010/0227755 | A1* | 9/2010 | Saito ...................... G01N 24/08 501/145 |

FOREIGN PATENT DOCUMENTS

| JP | 2012-184149 | 9/2012 |
| JP | 2015-17993 | 1/2015 |

* cited by examiner

*Primary Examiner* — Xiao S Zhao
*Assistant Examiner* — Ninh V Le
(74) *Attorney, Agent, or Firm* — Nixon & Vanderhye P.C.

(57) ABSTRACT

A method performs evaluation of properties of a clay rod, with which a honeycomb structural body is produced. The method mixes raw materials to produce a clay, and extrudes the clay and compresses the extruded clay to produce a clay rod. The method performs NMR to detect at least one of a T1 relaxation time and a T2 relaxation time in each of a normal part and an abnormality part extracted from the clay rod. Each of the T1 relaxation time and the T2 relaxation time corresponds to a relaxation time of nuclear spins of water protons magnetically excited in each of the normal part and the abnormality part. The method performs the evaluation of uniformity of a mixed state and a compression state of the clay rod based on a difference in T1 relaxation time and T2 relaxation time between the normal part and the abnormality part.

13 Claims, 9 Drawing Sheets

(51) Int. Cl.
*B28C 1/22* (2006.01)
*F01N 3/035* (2006.01)
*C04B 38/00* (2006.01)
*G01N 33/38* (2006.01)
*F01N 3/022* (2006.01)
*B01D 46/24* (2006.01)
*B28B 17/00* (2006.01)
*C04B 35/195* (2006.01)
*C04B 111/00* (2006.01)
*C04B 111/40* (2006.01)
*G01N 11/00* (2006.01)

(52) U.S. Cl.
CPC ............... *B28C 1/16* (2013.01); *B28C 1/227* (2013.01); *B28C 5/4286* (2013.01); *C04B 35/195* (2013.01); *C04B 38/0006* (2013.01); *C04B 38/0009* (2013.01); *F01N 3/0222* (2013.01); *F01N 3/035* (2013.01); *G01N 33/383* (2013.01); *B01D 2046/2496* (2013.01); *B01D 2279/30* (2013.01); *C04B 2111/0081* (2013.01); *C04B 2111/40* (2013.01); *C04B 2235/60* (2013.01); *C04B 2235/6021* (2013.01); *C04B 2235/61* (2013.01); *F01N 2330/04* (2013.01); *G01N 2011/0053* (2013.01)

(58) Field of Classification Search
CPC .. F01N 2330/04; G01N 33/383; G01N 33/38; G01N 24/08; G01N 24/085; G01R 33/50
See application file for complete search history.

FIG. 7(a) CLAY ROD PRODUCED BY PERFORMING MIXING PROCESS ONCE

FIG. 7(b) CLAY ROD PRODUCED BY PERFORMING MIXING PROCESS TWICE

FIG. 7(c) CLAY ROD PRODUCED BY PERFORMING MIXING PROCESS THREE TIMES

FIG. 7(d) CLAY ROD PRODUCED BY PERFORMING MIXING PROCESS ONCE WITH 10% INCREASED REDUCTION RATE R

EVALUATION METHOD FOR CLAY AND MANUFACTURING METHOD OF EXTRUSION MOLDED BODY

CROSS-REFERENCE TO RELATED APPLICATION

This application is related to and claims priority from Japanese Patent Application No. 2017-82908 filed on Apr. 19, 2017, the contents of which are hereby incorporated by reference.

BACKGROUND OF THE INVENTION

1. Field of the Invention

The present invention relates to evaluation methods performing evaluation of properties of clay and relates to manufacturing methods producing extrusion molded bodies to be used for manufacturing honeycomb structural bodies.

2. Description of the Related Art

There has been widely known and used a honeycomb structural body made of ceramics capable of purifying exhaust gas emitted from an internal combustion engine of a motor vehicle, etc. In general, a honeycomb structural body has cell walls and cells. The cell walls are arranged in a honeycomb structure on a cross section, which is perpendicular to an axial direction of, i.e. a longitudinal direction of the honeycomb structural body. Each of the cells is surrounded by the cell walls. That is, the cells, i.e. channels are arranged along an axial direction of the honeycomb structural body. Through the cells formed by the cell walls, exhaust gas emitted from an internal combustion engine flows and is purified. For example, the honeycomb structural body is produced by a following method.

In a first process, constituent components, at least ceramic raw material, binder, lubricant and water are mixed together to produce a clay. In a second process, the produced clay is extruded and molded to produce an extrusion molded body, i.e. a ceramic green body by using a die having a predetermined honeycomb structure. The extrusion molded body is dried and then fired to produce a honeycomb structural body.

The properties of the honeycomb structural body vary greatly due to the properties of the clay produced by the process previously described. However, in general, because the properties of the produced clay are evaluated in general by persons highly skilled in the art, this prevents stable supply of clay to be used for producing honeycomb structural bodies.

In order to solve the conventional problem, patent document 1, Japanese patent laid open publication No. 2010-208066, discloses a conventional evaluation method of evaluating the properties of a mixed state of clay and a conventional manufacturing method of manufacturing clay on the basis of the evaluation method. The conventional evaluation method uses a Nuclear Magnetic Resonance method (the NMR method) so as to detect a T1 relaxation time or/and a T2 relaxation time of nuclear spins of water protons magnetically excited in clay produced by using a pressure kneader. The patent document 1 discloses that it is possible to produce a honeycomb structural body without cracks, splits, etc. by lengthening the mixing period of time (in which the constituent components of the clay, i.e. ceramic raw material, binder, lubricant, water, etc. are mixed together,) to a time when the T1 relaxation time of nuclear spins of water protons magnetically excited in the clay becomes not more than 80% of an initial value of the T1 relaxation time of nuclear spins of water protons magnetically excited in the constituent components of the clay before the mixing process.

However, the conventional evaluation method and manufacturing method previously described cannot adequately suppress generation of defects from the produced honeycomb structure body and causes various limitations in actual use. That is, many actual manufacturing processes use screw extruder machines, called screw auger type molding machines, for extruding clay and molding honeycomb structural bodies instead of using pressure kneaders. It is difficult for such screw extruder machines to change the mixing period of time, in which the constituent components of the clay, i.e. ceramic raw material, binder, lubricant, water, etc. are mixed together. There is a strong demand of developing and providing an improved evaluation method of evaluating the properties of clay and an improved manufacturing method of preventing generation of defects from honeycomb structural bodies and of manufacturing the honeycomb structural bodies without structural detects.

The most important point to produce honeycomb structural bodies by using a screw extruder machine is to extrude clay at a constant extrusion speed on a cross section of a molded ceramic green body having a honeycomb structure. When the screw extruder machine cannot extrude a ceramic green body at a constant extrusion speed, cell distortion, cell-wall deformation such as waved cell walls, cracks, etc. are generated in the ceramic green body extruded from the screw extruder machine. The thinner the cell walls in the ceramic green body extruded by the screw extruder machine is, the more defects are generated in the ceramic green body.

In general, visual inspection can detect cell distortion and cracks generated in ceramic green bodies. However, such visual inspection cannot quantitatively detect generation of cell-wall deformation such as waved cell walls in ceramic green bodies. Accordingly, it is necessary to correctly produce honeycomb structural bodies without cell-wall deformations. When cell-wall deformations such as waved cell walls are formed in extruded bodies and the honeycomb structural body obtained from the extruded bodies, it is difficult for the cell walls to correctly and adequately support catalyst. This case generates an uneven catalyst layer, with which the inside of the cells, i.e. the cell walls of the produced honeycomb structural body are coated.

In order to uniformly extrude ceramic green bodies at a constant extrusion speed in the extrusion and molding process, it is important to use clay having uniform properties before mixing of constituent components of the clay, i.e. ceramic raw material, binder, lubricant, water, etc. However, the screw extruder machine often generates defects in extruded ceramic green bodies made of clay. Such defects are derived from the rotary motion of the screw due to the screw structure of the screw extruder machine. That is, it has been clear that such defects are generated due to the presence of a liquid component oozing from the clay on a screw surface of the screw extruder machine.

SUMMARY

It is therefore desired to provide an evaluation method performing quantitative evaluation of properties of extrusion molded bodies such as clay rods, detecting defects due to constituent components of the clay, a mixing state and a compression state of the extrusion molded bodies extruded from a screw extruder machine, and further desired to provide a manufacturing method of producing the extrusion molded bodies, i.e. ceramic green bodies made from the clay while suppressing generation of defects in honeycomb structural bodies made of the extrusion molded bodies.

In accordance with one aspect of the present invention, there is provided an evaluation method which performs evaluation of properties of an extrusion molded body made from a clay. The extrusion molded body is used for producing a honeycomb structural body.

The extrusion molded body is produced by mixing constituent components which contain at least ceramic raw material, binder, lubricant, water, etc. to produce a clay and by extruding the clay through a screw extruder machine, and by compressing the extruded clay through a resistant tube in the screw extruder machine to produce an extrusion molded body.

The evaluation method performs a pulse Nuclear Magnetic Resonance (NMR) to detect at least one of a T1 relaxation time of nuclear spins of water protons magnetically excited in a normal part in the extrusion molded body and a T2 relaxation time of nuclear spins of water protons magnetically excited in an abnormality part in the extrusion molded body.

The evaluation method performs evaluation of a uniformity of a mixed state and a compression state of the extrusion molded body on the basis of at least one of a difference in the T1 relaxation time between the normal part and the abnormality part, and a difference in the T2 relaxation time between the normal part and the abnormality part.

In accordance with another aspect of the present invention, there is provided a manufacturing method of producing an extrusion molded body. The produced extrusion molded body is used for manufacturing a honeycomb structural body. The manufacturing method performs a process of mixing constituent components which contain at least ceramic raw material, binder, lubricant and water to produce a clay. The manufacturing method further performs a process of extruding the clay by a screw extruder machine and of compressing an extruded clay through a resistant tube in the screw extruder machine so as to produce an extrusion molded body. The manufacturing method performs a process of performing a pulse Nuclear Magnetic Resonance to detect at least one of a T1 relaxation time of nuclear spins of water protons magnetically excited in a normal part in the extrusion molded body and a T2 relaxation time of nuclear spins of water protons magnetically excited in an abnormality part in the extrusion molded body. The manufacturing method performs a process of performing an evaluation of uniformity of a mixed state and a compression state of the extrusion molded body on the basis of at least one of a difference in the T1 relaxation time between the normal part and the abnormality part, and a difference in the T2 relaxation time between the normal part and the abnormality part. The manufacturing method further performs a process of determining a mixing condition in the mixing process and a compression condition in the extrusion process on the basis of at least one of a difference in the T1 relaxation time between the normal part and the abnormality part, and a difference in the T2 relaxation time between the normal part and the abnormality part.

As previously described, the evaluation method performs the mixing process, the extrusion process and the evaluation process. The mixing process mixes constituent components which contain at least ceramic raw material, binder, lubricant and water by using a mixing machine in a mixing and screw extruder machine M to produce a clay. The extrusion process extrudes the clay by using a screw extruder machine in the mixing and screw extruder machine M. The extrusion process further performs compression of the extruded clay by using a resistant tube arranged in the screw extruder machine to produce an extrusion molded body.

When the screw extruder machine performs inadequate extrusion and inadequate compression of the clay, a liquid component such as water is separated from the clay. The part containing the liquid component becomes the abnormality part. The evaluation process detects at least one of the T1 relaxation time of nuclear spins of water protons magnetically excited in the normal part in the clay, i.e. in the extrusion molded body, and the T2 relaxation time of nuclear spins of water protons magnetically excited in the abnormality part in the extrusion molded body. The evaluation method performs evaluation of uniformity of the mixed state and the compression state of the extrusion molded body on the basis of at least one of the difference in the T1 relaxation time between the normal part and the abnormality part, and the difference in the T2 relaxation time between the normal part and the abnormality part.

It is possible for the evaluation method according to one aspect of the present invention to perform the evaluation of quantitative uniformity of the mixed state and the compression state of the clay such as a clay rod on the basis of at least one of the difference of the T1 relaxation time and the difference of the T2 relaxation time. This makes it possible to defect defects of the clay, without depending on skilled workers, at an early stage in the manufacturing process of producing honeycomb structural bodies. This makes it possible to improve the yield rate of honeycomb structural bodies without defects.

Further, as previously described, the manufacturing method according to another aspect of the present invention performs the mixing process, the extrusion process and the evaluation process. That is, the manufacturing method determines the mixing condition used in the mixing process and the compression condition used in the extrusion process on the basis of at least one of the difference in T1 relaxation time between the normal part and the abnormality part, and the difference in T2 relaxation time between the normal part and the abnormality part. This makes it possible to obtain uniformity of properties of the extrusion molded body. To use the extrusion molded body produced by the method makes it possible to suppress defects from being generated in the honeycomb structural body.

As previously described, the present invention provides the evaluation method capable of quantitatively evaluating the state of defects generated in a clay, which has been produced, i.e. extruded and molded by using the screw extruder machine in the mixing and screw extruder machine. The present invention further provides the manufacturing method which manufacturing honeycomb structural bodies with less defects because of using the clay, for example, a clay rod which has been produced on the basis of the evaluation results of the evaluation method.

BRIEF DESCRIPTION OF THE DRAWINGS

A preferred, non-limiting embodiment of the present invention will be described by way of example with reference to the accompanying drawings, in which:

FIG. 7(a) shows a photograph of a cross section of the clay rod produced by performing the mixing process once;

FIG. 7(b) shows a photograph of a cross section of the clay rod produced by performing the mixing process twice;

FIG. 7(c) shows a photograph of a cross section of the clay rod produced by performing the mixing process three times; and FIG. 7(d) shows a photograph of a cross section of the clay rod produced by performing the mixing process once with 10% increased reduction rate R;

FIG. 10(a) shows a photograph showing the light transmittance of the honeycomb structural body made from the clay rod produced by performing the mixing process once;

FIG. 10(b) shows a photograph showing the light transmittance of the honeycomb structural body made from the clay rod produced by performing the mixing process twice;

FIG. 10(c) shows a photograph showing the light transmittance of the honeycomb structural body made from the clay rod produced by performing the mixing process three times; and FIG. 10(d) shows a photograph showing the light transmittance of the honeycomb structural body made from the clay rod produced by performing the mixing process once with 10% increased reduction rate R;

FIG. 11(a) shows a photograph showing an X-ray CT scan image of the honeycomb structural body made from the clay rod produced by performing the mixing process once;

FIG. 11(b) shows a photograph showing an X-ray CT scan image of the honeycomb structural body made from the clay rod produced by performing the mixing process twice;

FIG. 11(c) shows a photograph showing an X-ray CT scan image of the honeycomb structural body made from the clay rod produced by performing the mixing process three times; and FIG. 11(d) shows a photograph showing an X-ray CT scan image of the honeycomb structural body made from the clay rod produced by performing the mixing process once with 10% increased reduction rate R;

FIG. 12(a) is a photograph showing the difference d of variation of the catalyst coated depth W measured from the first end surface in the suction direction Xs of the honeycomb structural body made from the clay rod produced by performing the mixing process once;

FIG. 12(b) shows a photograph showing the difference d of variation of the catalyst coated depth W measured from the first end surface H7 in the suction direction Xs of the honeycomb structural body made from the clay rod produced by performing the mixing process twice;

FIG. 12(c) shows a photograph showing the difference d of variation of the catalyst coated depth W measured from the first end surface H7 in the suction direction Xs of the honeycomb structural body made from the clay rod produced by performing the mixing process three times;

FIG. 12(d) shows a photograph showing the difference d of variation of the catalyst coated depth W measured from the first end surface H7 in the suction direction Xs of the honeycomb structural body made from the clay rod produced by performing the mixing process once with 10% increased reduction rate R.

DETAILED DESCRIPTION OF THE PREFERRED EMBODIMENTS

Figure 1:
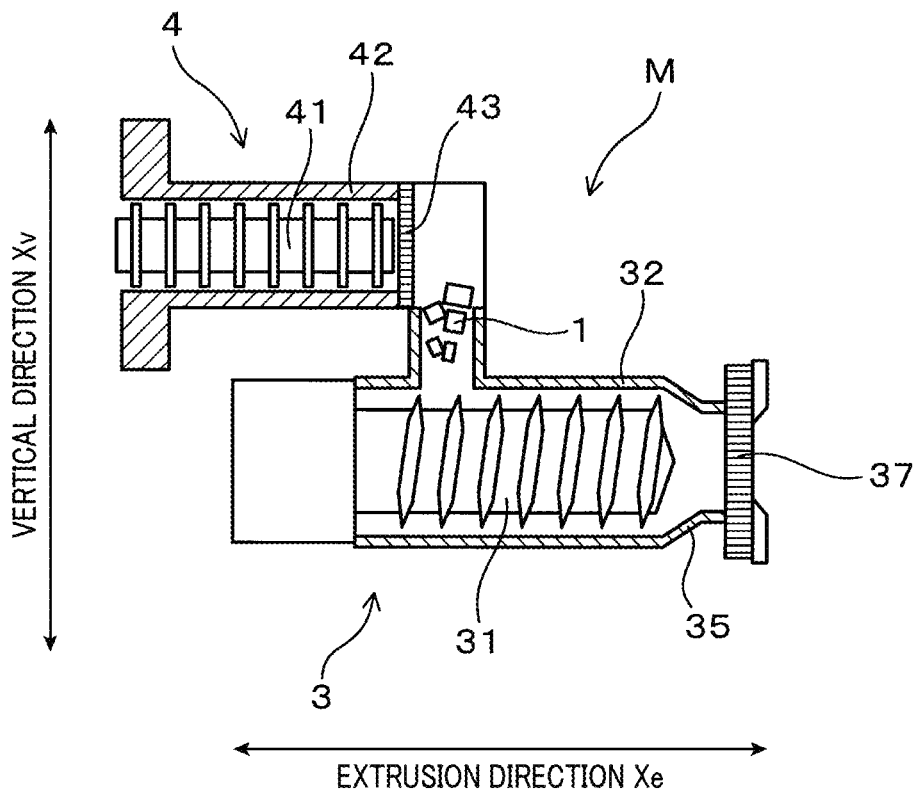
FIG. 1 is a view showing a schematic cross section of a mixing and screw extruder machine M composed of a screw extruder machine 3 and a mixing machine 4.

Hereinafter, various embodiments of the present invention will be described with reference to the accompanying drawings. In the following description of the various embodiments, like reference characters or numerals designate like or equivalent component parts throughout the several diagrams.

First Exemplary Embodiment

A description will be given of an evaluation method according to a first exemplary embodiment, which performs an evaluation process of evaluating a clay with reference to FIG. 1 to FIG. 5.

Figure 2:
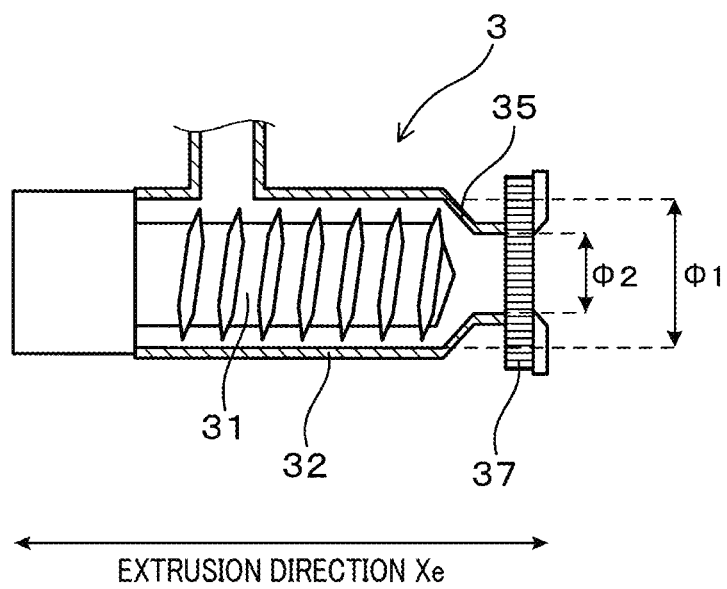
FIG. 2 is a view showing a schematic cross section of the screw extruder machine 3 in the mixing and screw extruder machine M shown in FIG. 1.

FIG. 1 is a view showing a schematic cross section of a mixing and screw extruder machine M composed of a screw extruder machine 3 and a mixing machine 4. FIG. 2 is a view showing a schematic cross section of the screw extruder machine 3 in the mixing and screw extruder machine M shown in FIG. 1. The mixing and screw extruder machine M produces a clay.

The evaluation method according to the first exemplary embodiment performs the evaluation process of evaluating various types of clay produced by the mixing and extrusion molding machine M. The clay is used for producing a honeycomb structural body.

A description will now be given of the evaluation method with reference to FIG. 1 to FIG. 5.

The clay is produced by the following processes. In a mixing process, the mixing machine 4 in the mixing and screw extruder machine M shown in FIG. 1 mixes constituent components such as ceramic raw material, binder, lubricant, water, etc. together to produce a clay. In an extrusion and molding process, the mixing and screw extruder machine M shown in FIG. 1 and FIG. 2 extrudes the produced clay to mold a ceramic green body. In drying and firing process, the produced ceramic green body is dried and then fired to produce the honeycomb structural body.

As shown in FIG. 1, the mixing and screw extruder machine M is composed of the mixing machine 4 and the screw extruder machine 3. Each of the mixing machine 4 and the screw extruder machine 3 has a single-axis type machine. However, it is acceptable to use a double axes type of each of the mixing machine 4 and the screw extruder machine 3. In view of easily visual inspection, it is preferable to use the mixing and screw extruder machine M composed of the screw extruder machine 3 of a single-axis type and the mixing machine 4a of a single-axis type. It is possible to easily and correctly detect an abnormality part, which is different from a normal part, in clay rods produced by the single-axis type of the screw extruder machine 3 and the mixing machine 4.

The mixing machine 4 has a mixing screw 41, a barrel 42 and a rectifying plate 43. For example, the barrel 42 has a cylindrical shape, which accommodates the mixing screw 41. The rectifier plate 43 is arranged at a front end of the barrel 42. The screw extruder machine 3 extrudes clay pellets of mixed constituent components, obtained by mixing ceramic raw material, binder, lubricant, water, etc., through the rectifying plate 43.

The screw extruder machine 3 has an extrusion screw 31, a barrel 32, a resistant tube 35, and a metal die 37. For example, the barrel 32 has a cylindrical shape, which accommodates the extrusion screw 31. The resistant tube 35 is arranged at a front end of the barrel 32. The resistant tube 35 has a reduced-diameter part of a cylindrical shape. A diameter of the resistant tube 35 is gradually reduced toward the front end part thereof. The metal die 37 has a honeycomb-shaped slit.

It is possible for at least one of the mixing screw 41 and the barrel 42 in the mixing machine 4 to have a cooling tube through which a coolant flows. That is, it is possible to detect a temperature of constituent components of the clay in the mixing machine 4.

In addition, it is possible for at least one of the extrusion screw 31 and the barrel 32 in the screw extruder machine 3 to have a cooling tube through which a coolant flows. That is, it is possible to detect a temperature of the clay in the screw extruder machine 3. The cooling tube in the screw extruder machine 3 and the cooling tube in the mixing machine 4 are omitted from FIG. 1 and FIG. 2.

As shown in FIG. 1, in the structure of the mixing and screw extruder machine M, the screw extruder machine 3 and the mixing machine 4 are stacked in the vertical direction Xv shown in FIG. 1. The mixing machine 4 is arranged on the screw extruder machine 3 in the vertical direction Xv. For example, Universe Inc. in Japan produces and provides such a mixing and screw extruder machine M. In the structure of the mixing and screw extruder machine M shown in FIG. 1, the mixing machine 4 supplies clay pellets as the clay 1 through the rectifying plate 43. The clay pellets as the clay 1 themselves drop by gravity into the screw extruder machine 3.

In the screw extruder machine 3, the clay pellets as the clay 1 supplied from the mixing machine 4 are rotated and transmitted as the clay by the extrusion screw 31 to the resistant tube 35. The clay is compressed by the resistant tube 35 when the clay is passing there through. That is, the resistant tube 35 compresses the clay and to produce an extrusion molded body, and a honeycomb structural body is produced through the metal die 37. The honeycomb molded body is supplied to the outside of the mixing and screw extruder machine M.

In the screw extruder machine 3 shown in FIG. 1 and FIG. 2, the resistant tube 35 is arranged between the barrel 32 and the metal die 37. The resistant tube 35 has the reduced-diameter part of a cylindrical shape. For example, when the resistant tube 35 has a cylindrical shape, the clay supplied through the resistant tube 35 is pressed and shaped as a clay rod, and the clay rod is supplied into the metal die 37.

It is possible to change a reduction rate R of the resistant tube 35 and an extrusion length of the resistant tube 35, respectively. This makes it possible to adjust the pressed condition of the clay rods.

It is possible to calculate the reduction rate R by the following equation (I):

$$R = (\phi 1 - \phi 2) \times 100 / \phi 1 \qquad (I),$$

where $\phi 1$ indicates an inlet diameter of the resistant tube 35 and $\phi 2$ indicates an outlet diameter of the resistant tube 35. FIG. 2 shows the inlet diameter $\phi 1$ and the outlet diameter $\phi 2$.

The clay rod is supplied to and passes through the metal die 37 which has slits (not shown) so as to produce a honeycomb molded body. The metal die 37 is arranged at the front end of the resistant tube 35. The honeycomb molded body is cut by a predetermined length, and then dried and fired to produce honeycomb structural bodies.

Clay is produced by a mixture of constituent components such as ceramic raw material, binder, lubricant, water, etc. It is possible to use, as the ceramic raw material, cordierite obtained by firing a cordierite raw material. The cordierite raw material is a mixture of alumina, aluminum hydroxide, silica, talc, kaolin, etc.

In general, a honeycomb structural body is made of cordierite, SiC, aluminum titanate, zeolite, a composite material of alumina and ceria zirconia, and titania. It is possible to use ceramic raw material composed of them. It is preferable to use cordierite having a low thermal expansion coefficient.

It is possible to use, as binder, methyl cellulose, hydroxypropyl methyl cellulose, hydroxypropyl methylcellulose, hydroxyethyl cellulose, carboxymethyl cellulose, silica sol, alumina sol, etc.

It is possible to use, as lubricant, oleic acid, linoleic add, linseed oil, rapeseed oil, and Unilube, etc. produced by NOF CORPORATION. It is possible to use canola oil as rapeseed oil. It is acceptable to use grease or emulsifier as lubricant of commercial products.

It is preferable for vegetable oil such as linseed oil and rapeseed oil to contain triacylglycerol. It is preferable for fatty acid forming triacylglycerol to have 18 carbon atoms. For example, there are, as the fatty acid, stearic acid, oleic acid, linoleic acid, elaidic acid, cis-vaccenic acid, vaccenic acid, etc. It is possible to use lubricant to improve a molding speed or a shaping speed.

(Evaluation of Clay)

A description will now be given of the evaluation method according to the first exemplary embodiment with reference to FIG. 3 to FIG. 5.

Figure 3:
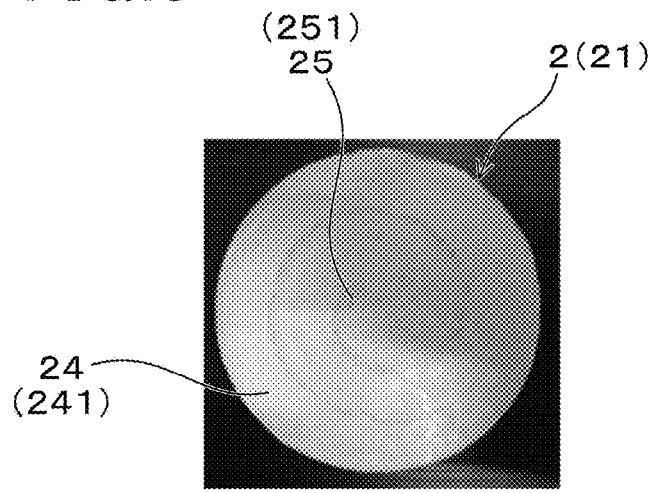
FIG. 3 is a view showing a photograph of a cross section of an extrusion molded body 2 as a clay rod 21 having a rod shape produced before passing through a metal die 37, which is perpendicular to an axial direction of the extrusion molded body 2 as the clay rod 21.

FIG. 3 is a view showing a photograph of a cross section of an extrusion molded body 2 as a clay rod 21 having a rod shape obtained before a metal die 37. The cross section shown in FIG. 3 is perpendicular to an axial direction of the extrusion molded body 2 as the clay rod 21. FIG. 4 is a view showing a photograph of a cross section of a cut product having a predetermined length obtained by cutting the honeycomb molded body 22 into plural products, in a cutting direction which is perpendicular to the axial direction of the honeycomb molded body 22.

That is, the honeycomb molded body 22 supplied through the metal die 37 is cut into a plurality of cut products. Each of the cut products has a predetermined length. The cross section shown in FIG. 4 is perpendicular to the axial direction of the honeycomb molded body 22.

Figure 4:
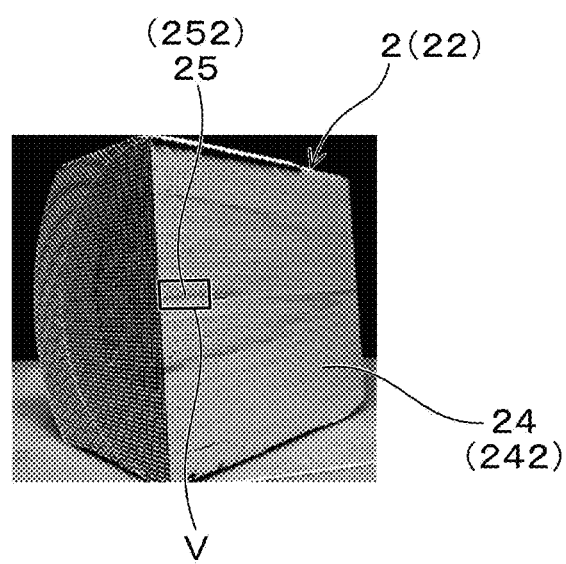
FIG. 4 is a view showing a photograph of a cross section of a cut product having a predetermined length obtained by cutting the honeycomb molded body 22 into plural products, in a cutting direction which is perpendicular to the axial direction of the honeycomb molded body 22.
Figure 5:
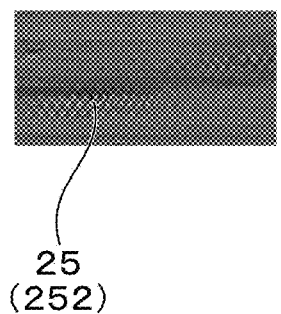
FIG. 5 is an enlarged view of a region V shown in the photograph of the cross section of the honeycomb molded body 22 shown in FIG. 4.

FIG. 5 is an enlarged view of a region V shown in the photograph of the cross section of the honeycomb molded body 22 shown in FIG. 4.

The evaluation method according to the first exemplary embodiment evaluates extrusion molded bodies 2 shown in FIG. 3 and FIG. 4 produced by changing production conditions performed by the mixing and screw extruder machine M shown in FIG. 1.

The evaluation method according to the first exemplary embodiment performs a pulse Nuclear Magnetic Resonance (pulse NMR) to detect a T1 relaxation time of nuclear spins of water protons magnetically excited in each of the extrusion molded bodies 2. It is possible to detect a T2 relaxation time of nuclear spins of water protons magnetically excited in each of the extrusion molded bodies 2 instead of detecting the T1 relaxation time. It is also possible to detect both the T1 relaxation time and the T2 relaxation time of water protons magnetically excited in each of the extrusion molded bodies 2.

It is acceptable to use, as the extrusion molded bodies 2, the clay rods 21 and the honeycomb molded bodies 22. In the first exemplary embodiment, the extrusion molded body 2 includes the clay rod 21 and the honeycomb molded body 22. This makes it possible to correctly evaluate a mixed state and a compressive state of each of the extrusion molded bodies 2. The cut product of the honeycomb molded body 22 shown in FIG. 4 has been cut from the honeycomb molded body 22 supplied through the metal die 37 in the screw extruder machine 3 shown in FIG. 2. That is, the honeycomb molded bodies 22 shown in FIG. 4 have the same as shape of the honeycomb structural body shown in FIG. 6 manufactured by the manufacturing method according to the second exemplary embodiment which will be described later.

An inadequate mixing process may generate a clay having a spiral pattern, for example, as shown in FIG. 3, around a central portion on a cross section of the clay rod 21 as the extrusion molded body 2. The spiral pattern on a cross section of the clay rod 21 is generated due to a rotational motion of the extrusion screw 31 of the screw extruder machine 3. On the spiral pattern shown in FIG. 3, a black color is gradually changed to a dark gray color. That is, the spiral pattern corresponds to an abnormality part 25 and the area without the spiral pattern corresponds to a normal part 24. In FIG. 3, the area from the black colored area to the dark gray colored area corresponds to the abnormality part 25, and the area from the white colored area to the light gray colored area corresponds to the normal part 24.

In FIG. 3, the abnormality part 25 is a lamination part 251 from which water has been separated. The normal part 24 is a non-lamination part 241 with water. It is possible to detect the presence of each of the normal part 24 and the abnormality part 25 by visual inspection, for example.

It is preferable for a clay to contain at least talc as the ceramic raw material in view of performing the easy visual inspection. In this case, because the abnormality part 25 has a black color due to the mixture of talc, lubricant and water, it is possible to easily perform the visual inspection to detect the presence of the abnormality part 25 in the clay rod 21.

When using an auger screw molding machine as a screw extruder machine, the abnormality part 25 composed of the lamination part 251 is usually generated if abnormalities occur. However, this often causes a difficulty in performing the visual inspection based on a light and shade pattern. In this case, it is possible to use the following detection method of distinguishing the normal part 24 from the abnormality part 25.

For example, there is a method of eliminating water from an extrusion molded body such as the clay rod 21 by using a drying machine. Because this method generates cracks in the abnormality part 25, it is possible to detect the presence of the abnormality part 25 with high accuracy. That is, after the drying process, such cracks are generated in the abnormality part 25 only. No crack is generated in the normal part 24. In the abnormality part 25, a clay component is not adequately compressed, and cracks are generated in the abnormality part 25 by the drying process.

There is another detection method to quickly cool the extrusion molded body as the clay rod 21, etc. That is, the rapid cooling expands a volume of water component in the extrusion molded body, and generates cracks therein. After the rapidly cooling, such cracks are generated in the abnormality part 25 only. No crack is generated in the normal part 24.

As previously described, the extrusion molded body 2 is used as a detection target having a rod shape made of a compressed clay so as to detect the presence of the normal part 24 and the abnormality part 25. However, the concept of the present invention is not limited by this. For example, it is acceptable to use the honeycomb molded body 22 shown in FIG. 4 produced through the metal die 37 arranged in the screw extruder machine 3 of the mixing and screw extruder machine M. It is possible to detect a waved part 252 and a non-waved part 242 when the honeycomb molded body 22 is used as the detection target. That is, the waved part 252 corresponds to the abnormality part 25, and the non-waved part 242 corresponds to the normal part 24.

The honeycomb molded body 22 shown in FIG. 4 and FIG. 5 has been dried so as to highlight the abnormality part 25 from the normal part 24.

It is acceptable to add liquid colorant to clay so as to color the clay and to visually detect the change of raw material, product units or a composition of the raw material. This coloring easily distinguishes the abnormality part 25 from the normal part 24. The stronger colored area corresponds to the abnormality part 25, and the light colored area corresponds of the normal part 24. As previously described, it is possible to color the clay in view of clearly distinguishing the abnormality part 25 from the normal part 24 in the extrusion molded body 2 as the detection target.

Because the abnormality part 25 contains lubricant in addition to water, it is possible to perform the detection of each of the abnormality part 25 and the normal part 24 with high accuracy by using a FT-IR (a Fourier transform infrared spectrophotometer). In this case, a relatively strong peak derived from a lubricant component in a detection result of the FT-IR corresponds to the abnormality part 25, and a relatively weak peak corresponds to the normal part 24.

It is possible to use an NMR analyzer such as an Acorn Area manufactured by XiGo Nanotools, Inc. For example, the NMR (nuclear magnetic resonance) is measured with 14 MHz electromagnetic wave pulses at a temperature of 25° C. A test tube is filled with a small amount of each of the abnormality part 25 and the normal part 24 in the extrusion molded body 2. A pulse NMR method detects a T1 relaxation time and a T2 relaxation time of nuclear spins of water protons magnetically excited in each test tube filled with the normal part 24 and the abnormality part 25.

It is possible to distinguish water molecules on the raw material of the clay (i.e. of the extrusion molded body 2) from water molecules present in a bulk on the basis of at least one of the T1 relaxation time and the T2 relaxation time detected by using the NMR analyzer. Specifically, when water molecules are adhered on the surface of the raw materials forming the extrusion molded body 2, each of the T1 relaxation time and the T2 relaxation time is reduced. On the other hand, when water molecules are present in the bulk, each of the T1 relaxation time and the T2 relaxation time increases.

The water molecules contained in the abnormality part 25 are present in the bulk because water molecules have been separated from the abnormality part 25 at a high pressure. As a result, each of the T1 relaxation time and the T2 relaxation time is reduced in the abnormality part 25. On the other hand, because water molecules contained in the normal part 24 are chemically-adsorbed water molecules, each of the T1 relaxation time and the T2 relaxation time increases.

Accordingly, it is possible to detect the mixed state of the raw materials and the compressed state of the clay on the basis of a difference between the T1 relaxation time and the T2 relaxation time. In other words, the smaller the difference between the T1 relaxation time and the T2 relaxation time is, the more the mixed state of the raw materials and the compressed state of the clay adequately increase.

As previously described in detail, the evaluation method according to the first exemplary embodiment performs the mixing process, the extrusion process, and evaluation process.

In the mixing process, for example, the mixing screw 41 in the mixing machine 4 shown in FIG. 1 mixes the constituent components, i.e. ceramic raw material, binder, lubricant, water, etc. are mixed together to produce the clay 1. In the extrusion process, the screw extruder machine 3 extrudes and molds the clay 1 to produce the extrusion molded body 2 made of the clay 1 (see FIG. 3 to FIG. 5) through the resistance tube 35.

As shown in FIG. 1, when the screw extruder machine 3 extrudes the clay 1, liquid component such as water is separated from the extrusion molded body. Insufficient mixing and/or insufficient compressing causes the generation of a large amount of liquid component such as water from the extrusion molded body 2.

As shown in FIG. 3 to FIG. 5, the generated liquid component corresponds to the abnormality part 25, and the clay containing the water component corresponds to the normal part 24. It is possible to usually detect each of the normal part 24 and the abnormality part 25 by using the visual inspection. That is, in the visual inspection, the dark colored part corresponds to the abnormality part 25, and the light colored part corresponds to the normal part 24.

The evaluation process detects at least one of the T1 relaxation time of nuclear spins of water protons magnetically excited in each of the normal part 25 and the abnormality part 24 in each test sample as the extrusion molded body 2 made of the clay 1. The evaluation process makes it possible to detect a degree of uniformity in the mixed state and the compressed state of the clay 1 as each of the test samples extruded under various conditions from the mixing and screw extruder machine M composed of the screw extruder machine 3 and the mixing machine 4.

That is, the evaluation process in the evaluation method according to the first exemplary embodiment can quantitatively evaluate the uniformity in mixed state and compressed state of the normal part 24 and the abnormality part 25 of the clay on the basis of at least one of a difference in the T1 relaxation time between the normal part 24 and the abnormality part 25 in each test sample, and a difference in the T2 relaxation time between the normal part 24 and the abnormality part 25 in each test sample. This makes it possible to detect defects of the clay 1, without depending on skilled workers, at an early state in the manufacturing process of producing honeycomb structural bodies. This makes it possible to improve the yield rate of honeycomb structural bodies without defects.

It is possible to apply the evaluation method according to the first exemplary embodiment previously described to a time at the introduction of equipment to a factory, to a time when a production lot is changed, to a time when a composition of the raw material is changed, etc. It is possible for the evaluation method according to the first exemplary embodiment to adjust the T1 relaxation time and the T2 relaxation time of each of the normal part 24 and the abnormality part 24 in a test sample by changing the mixed state and the compressed state of the test sample on the basis of the evaluation results. Specifically, it is possible for the evaluation method according to the first exemplary embodiment to adjust the T1 relaxation time and the T2 relaxation time of each test sample by changing a temperature of a coolant which flows in the inside of the mixing machine 4, a length in the extrusion direction of the resistant tube 35, a reduction rate of the resistant tube 35, the number of times of the mixing, etc. This makes it possible to manufacture honeycomb structural bodies with less defects while improving the yield rate of the honeycomb structural bodies.

Second Exemplary Embodiment

A description will be given of the manufacturing method according to a secondary exemplary embodiment with reference to FIG. 6 to FIG. 13. The manufacturing method according to the secondary exemplary embodiment manufactures extruded bodies and honeycomb structural bodies. The same components used in the second exemplary embodiment and the first exemplary embodiment will be referred with the same reference numbers and characters.

Figure 6:
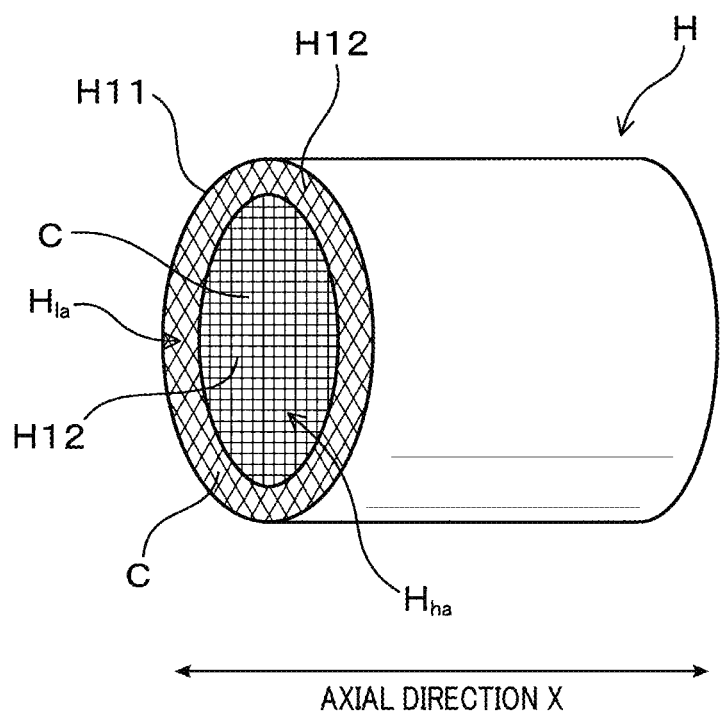
FIG. 6 is a perspective view showing a structure of a honeycomb structural body H produced by a manufacturing method according to a second exemplary embodiment of the present invention.

FIG. 6 is a perspective view showing a structure of a honeycomb structural body H produced by the manufacturing method according to the second exemplary embodiment. That is, the honeycomb structural body H shown in FIG. 6 basically corresponds to the cut product shown in FIG. 4. As shown in FIG. 6, the honeycomb structural body H has an outer skin part H11, a plurality of cell walls H12 having a porous structure, and a plurality of cells C which are formed along the axial direction X of the honeycomb structural body H. The outer skin part H11 has a cylindrical shape.

On a cross section of the honeycomb structural body H, which is perpendicular to the axial direction X of the honeycomb structural body H, the inside area of the outer skin part H11 is divided into a plurality of areas by the cell walls H12. In other words, each of the cells C is surrounded by the cell walls H12. Exhaust gas, emitted from an internal combustion engine, is passing through the cells C. That is, the cells C form exhaust gas passages.

As shown in FIG. 6, it is possible to divide the overall area on a cross section of the honeycomb structural body H into plural regions having different cell sizes, respectively. The overall area on the cross section shown in FIG. 6 is divided into two regions, the inside region $H_{ha}$ and the outside region $H_{lo}$. For example, the cells C is arranged at a first cell density in the inside region $H_{ha}$, and the cells C is arranged at a second cell density in the outside region $H_{lo}$. The first cell density of the inside region $H_{ha}$ is higher than the second cell density of the outside region $H_{lo}$. As shown in FIG. 6, a boundary wall H15 is formed between the inside region $H_{ha}$ and the outside region $H_{lo}$. It is acceptable to produce the honeycomb structural body H without the boundary wall H15. It is also acceptable to produce the honeycomb structural body H having a single cell density region, i.e. having a single region of a uniform cell density in the inside of the outer skin part H11.

The manufacturing method according to the second exemplary embodiment performs the mixing process, extrusion process, and the evaluation process so as to produce the extrusion molded body. Further, the manufacturing method according to the second exemplary embodiment performs the drying process and the firing process to manufacture the honeycomb structural body H. It is possible for the mixing process and the extrusion process to use the mixing and screw extruder machine M shown in FIG. 1.

The mixing process mixes ceramic raw materials, binder, lubricant and water to produce a mixture thereof, and to supply the clay 1. In the extrusion process The mixing process mixes uses the mixing machine 4 in the mixing and screw extruder machine M shown in FIG. 1 to produce a mixture of constituent components containing at least ceramic raw material, binder, lubricant and water, and to supply the clay 1.

The extrusion process uses the screw extruder machine 3 shown in FIG. 2 extrudes the clay 1 and compresses the extruded clay 1 through the resistant tube 35, and supplies the extrusion molded body as the clay rod 21.

The manufacturing method according to the second exemplary embodiment uses, as the ceramic row material, cordierite raw materials which will become cordierite after the firing process. Specifically, the manufacturing method according to the second exemplary embodiment used the ceramic row materials made of alumina, aluminum hydroxide, silica, talc, kaolin, etc. The manufacturing method according to the second exemplary embodiment used methyl cellulose at 4.5 wt % as binder, and used water at 20 wt %. The manufacturing method according to the second exemplary embodiment further used lubricant at 1.8 wt % which contains oleic acid, linoleic acid, etc.

Those ceramic raw materials, the binder, water and the lubricant were inserted into the mixing and screw extruder machine M, and mixed and compressed them so as to produce honeycomb molded bodies, similar to the first exemplary embodiment previously described. In the second exemplary embodiment, the clay pellets as the clay 1 supplied from the rectifying plate 43 in the mixing machine 4 were inserted again into the mixing machine 4. After this repetition within a range of one to three times of the mixing process, the clay pellets as the clay 1 were supplied into the screw extruder machine 3 to produce the honeycomb molded bodies 22.

The manufacturing method according to the second exemplary embodiment used, as a clay sample having the normal part 24 and the abnormality part 25, the clay rod 21 before passing through the metal die 37.

The second exemplary embodiment prepared the clay samples of the normal part 24 and the abnormality part 25 made of the clay 1 obtained by the repetition of the mixing process performed by one to three times. The second exemplary embodiment used test tubes of a normal type to be used for ACORN DROP measurement manufactured by Nihon Rufuto Co. Ltd.

The second exemplary embodiment performed the NMR method to detect the T1 relaxation time and the T1 relaxation time of nuclear spins of water protons magnetically excited in each of the test tubes. The second exemplary embodiment performed the NMR method with 14 MHz electromagnetic wave pulses at a temperature of 25° C. The second exemplary embodiment performed the above measurements of each of the test tubes twice, and calculated an average value of the detected T1 relaxation time and the detected T2 relaxation time of each of the test tubes.

Figure 7:
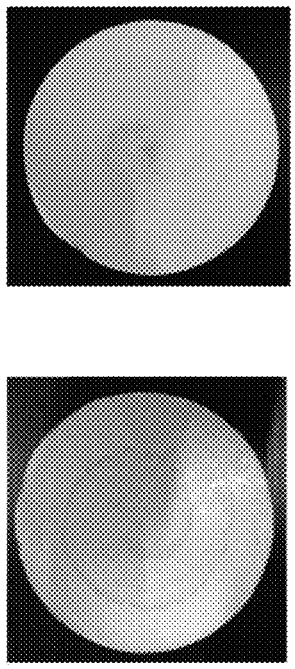
FIG. 7(a) to FIG. 7(d) are views showing photographs of a cross section of each of clay rods as test samples produced by the manufacturing method according to the second exemplary embodiment, in particular.

FIG. 7(*a*) to FIG. 7(*d*) are views showing photographs of a cross section of each of clay rods obtained by the manufacturing method according to the second exemplary embodiment.

In particular, FIG. 7(*a*) shows a photograph of a cross section of the clay rod produced by performing a mixing process once. FIG. 7(*b*) shows a photograph of a cross section of the clay rod produced by performing a mixing process twice. FIG. 7(*c*) shows a photograph of a cross section of the clay rod produced by performing a mixing process three times.

The manufacturing method according to the second exemplary embodiment detected the relationship between the number of times of performing the mixing process, the reduction rate R and the T1 relaxation time, and the relationship between the number of times of performing the mixing process, the reduction rate R and the T2 relaxation time.

Figure 8:
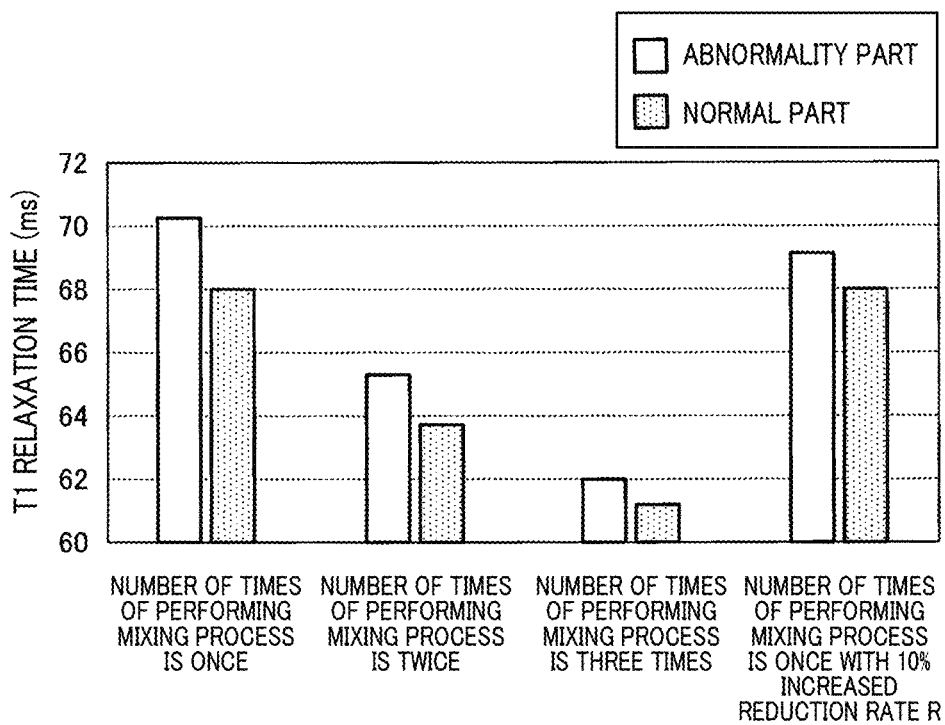
FIG. 8 is a graph showing a relationship between the number of times of performing the mixing process, the reduction rate R and the T1 relaxation time of nuclear spins of water protons, magnetically excited, in a defect part and a normal part in each of test samples (clay rods) detected by the manufacturing method according to the second exemplary embodiment of the present invention.
Figure 9:
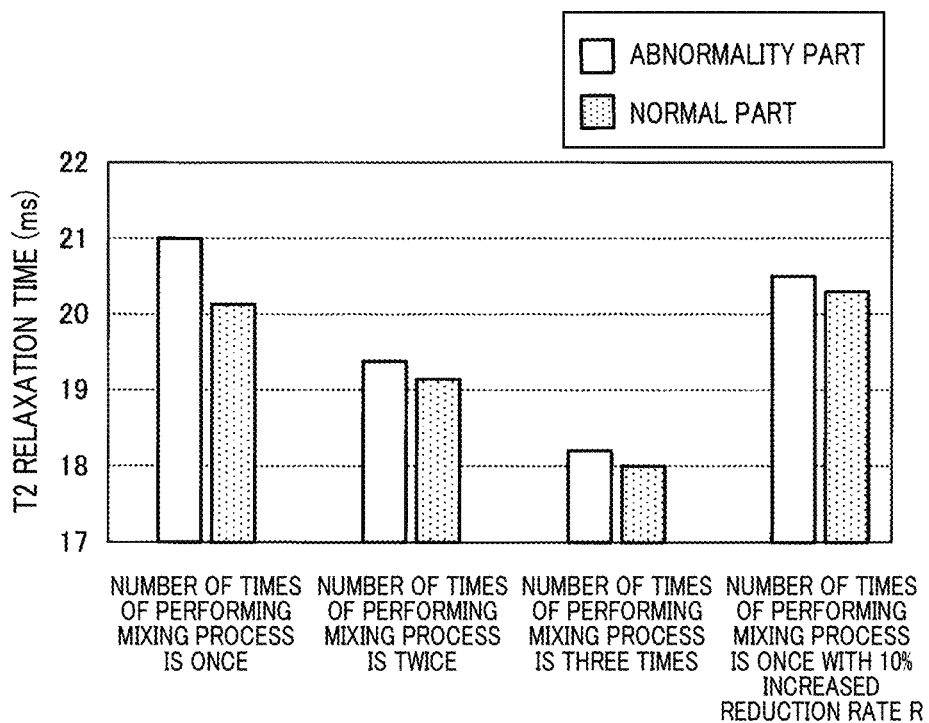
FIG. 9 is a graph showing a relationship between the number of times of performing the mixing process, the reduction rate R and the T2 relaxation time of nuclear spins of water protons, magnetically excited, in a defect part and a normal part in each of test samples (clay rods) detected by the manufacturing method according to the second exemplary embodiment of the present invention.

That is, FIG. 8 is a graph showing the relationship between the number of times of performing the mixing process, the reduction rate R and the T1 relaxation time of nuclear spins of water protons magnetically excited in a defect part and a normal part in each of the clay rods as the test samples. Similarly, FIG. 9 is a graph showing the relationship between the number of times of performing the mixing process, the reduction rate R and the T2 relaxation time of nuclear spins of water protons magnetically excited in a defect part and a normal part in each of the clay rods as the test samples.

In particular, the clay rod as the test sample shown in FIG. 7 (*d*) and the honeycomb molded body by using the clay rod shown in FIG. 7 (*d*) were produced by performing the mixing process once with 10% increased reduction rate R. The second exemplary embodiment also detected the T1 relaxation time (see FIG. 8) and the T2 relaxation time (see FIG. 9) of the clay rod shown in FIG. 7(*d*).

It is possible to calculate a difference ΔT1(%) between a T1 relaxation time $N_{T1}$ (ms) of the normal part and a T1 relaxation time $A_{T1}$ (ms) of the abnormality part in each test sample by the following equation (II).

$$\Delta T1(\%) = (A_{T1} - N_{T1})/A_{T1} \times 100 \quad (II).$$

In addition, it is possible to calculate a difference ΔT2(%) between a T2 relaxation time $N_{T2}$ (ms) of the normal part and a T2 relaxation time $A_{T2}$ (ms) of the abnormality part in each test sample by the following equation (III).

$$\Delta T2(\%) = (A_{T2} - N_{T2})/A_{T2} \times 100 \quad (III).$$

Table 1 shows the calculation results of the test samples.

TABLE 1

| The number of times of mixing process | Increased rate (%) of reduction rate R | ΔT1 (%) | ΔT2 (%) |
|---|---|---|---|
| 1 | 0 | 3.2 | 4.2 |
| 2 | 0 | 2.3 | 1.3 |
| 3 | 0 | 1.3 | 1.1 |
| 1 | 10 | 1.7 | 1.1 |

Next, the second exemplary embodiment detected the presence of defects in each of honeycomb structural bodies as test sample. Those test samples have been made from the clay rods shown in FIG. 7(a) to FIG. 7(d) which have been produced by changing the number of times of the mixing process and the reduction rate R as previously described. Specifically, the second exemplary embodiment performed the light transmittance test, the X-ray CT scan test, and the catalyst coating test for each of the test samples so as to detect the presence of defects in each of the test samples.

(Light Transmittance Test)

FIG. 10(a) to FIG. 10(d) are photographs showing the light transmittance of each of the honeycomb structural bodies as the test samples produced by the manufacturing method according to the second exemplary embodiment. In more detail, FIG. 10(a) shows a photograph which shows the light transmittance of the honeycomb structural body made from the clay rod produced by performing the mixing process once. FIG. 10(b) shows a photograph which shows the light transmittance of the honeycomb structural body made from the clay rod produced by performing the mixing process twice. FIG. 10(c) shows a photograph which shows the light transmittance of the honeycomb structural body made from the clay rod produced by performing the mixing process three times. FIG. 10(d) shows a photograph which shows the light transmittance of the honeycomb structural body made from the clay rod produced by performing the mixing process once with 10% increased reduction rate R.

Figure 10:
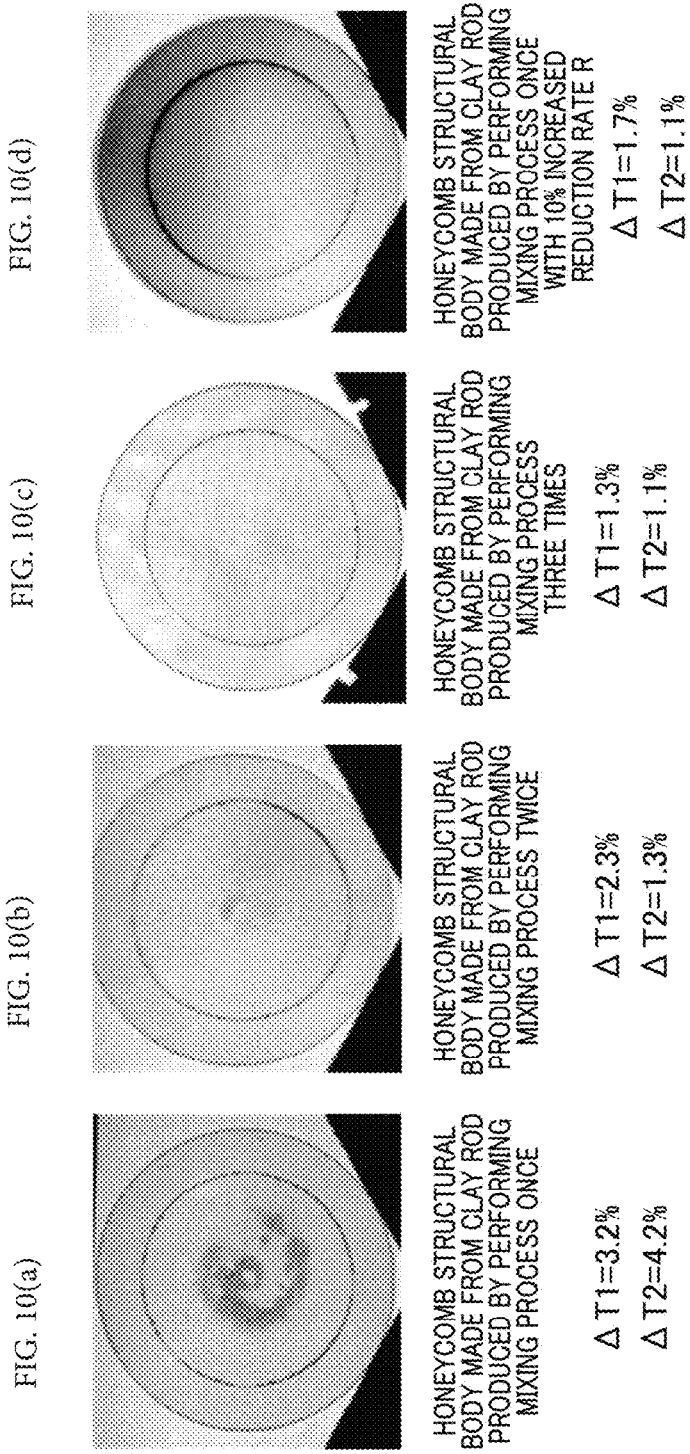
FIG. 10(a) to FIG. 10(d) are photographs showing a light transmittance of each of honeycomb structural bodies as test samples produced by the manufacturing method according to the second exemplary embodiment, in particular.
Figure 11:
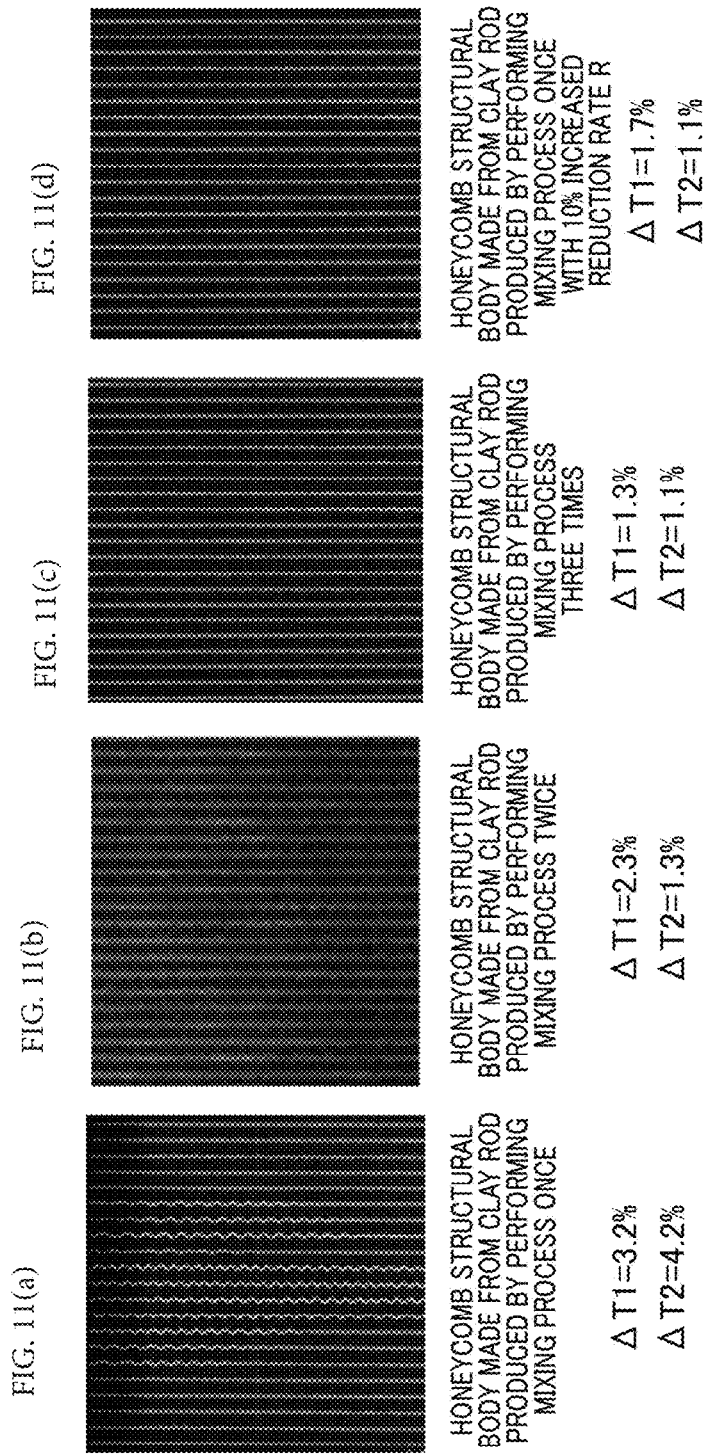
FIG. 11(a) to FIG. 11(d) are photographs showing an X-ray CT scan image of each of the honeycomb structural bodies as the test samples produced by the manufacturing method according to the second exemplary embodiment, in particular.
Figure 12:
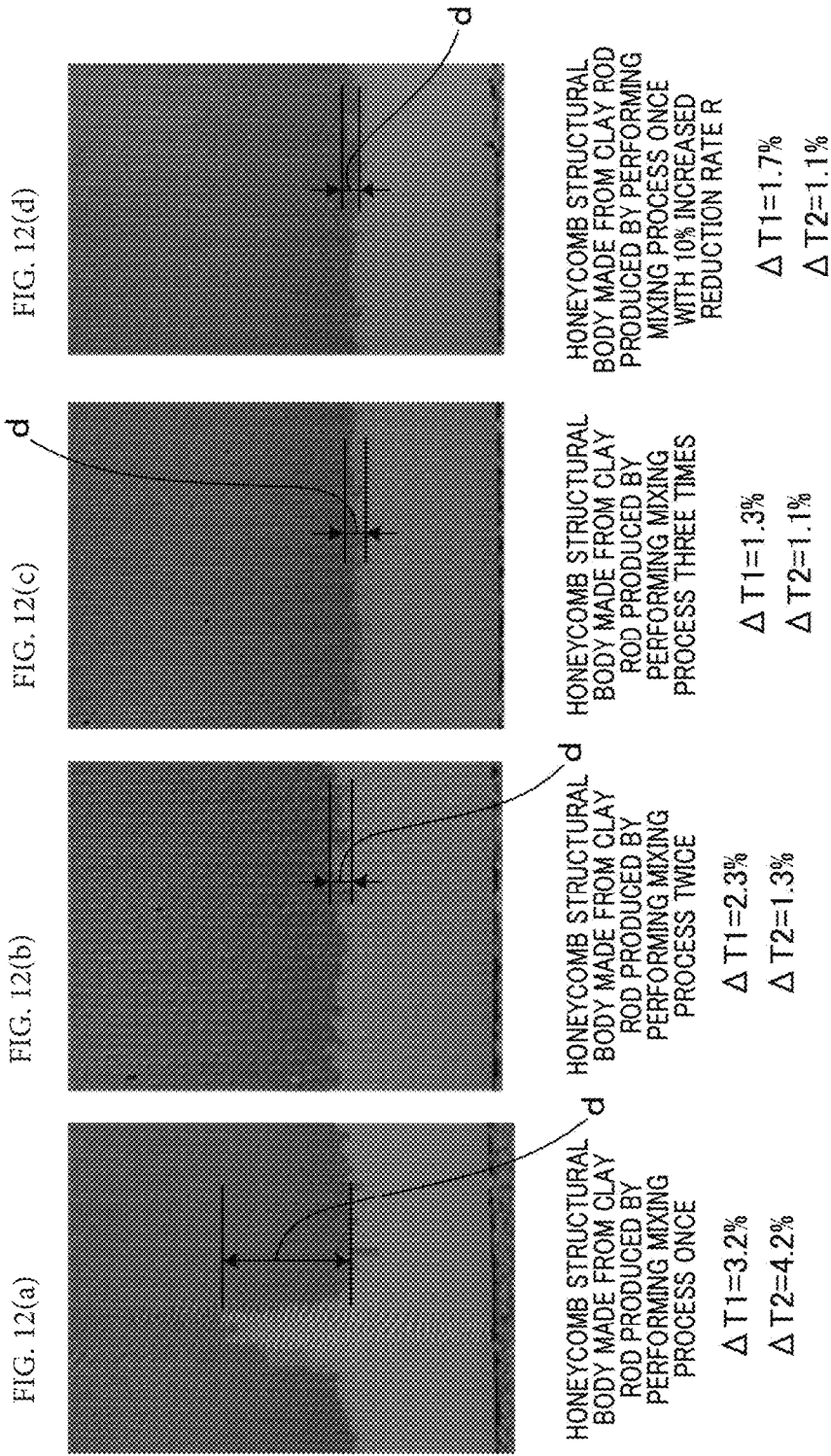
FIG. 12(a) to FIG. 12(d) are photographs showing a difference d of variation of the catalyst coated depth W measured from the first end surface H7 in the suction direction Xs of each of the honeycomb structural bodies as the test samples produced by the manufacturing method according to the second exemplary embodiment, in particular.

A black shade area in each of the photographs shown in FIG. 10 (a) to FIG. 10 (d) represents deformation of cell walls such as waved cell walls, cracks, etc.

(X-Ray CT Scan Test)

The second exemplary embodiment performed the X-ray CT scan test to detect the presence of waved cell walls in each of the honeycomb structural bodies as the test samples.

FIG. 11(a) to FIG. 11(d) are photographs showing a X-ray CT scan image of each of the honeycomb structural bodies as the test samples produced by the manufacturing method according to the second exemplary embodiment. In more detail, FIG. 11(a) shows a photograph which shows the X-ray CT scan image of the honeycomb structural body made from the clay rod produced by performing the mixing process once. FIG. 11(b) shows a photograph which shows the X-ray CT scan image of the honeycomb structural body made from the clay rod produced by performing the mixing process twice. FIG. 11(c) shows a photograph which shows the X-ray CT scan image of the honeycomb structural body made from the clay rod produced by performing the mixing process three times. FIG. 11(d) shows a photograph which shows the X-ray CT scan image of the honeycomb structural body made from the clay rod produced by performing the mixing process once with 10% increased reduction rate R. The second exemplary embodiment used SMX-225CT as the X-ray scan device manufactured by the SHIMADZU CORPORATION.

(Catalyst Coating Test)

The second exemplary embodiment performed the catalyst coating test which sucks catalyst slurry having thixotropy property.

Figure 13:
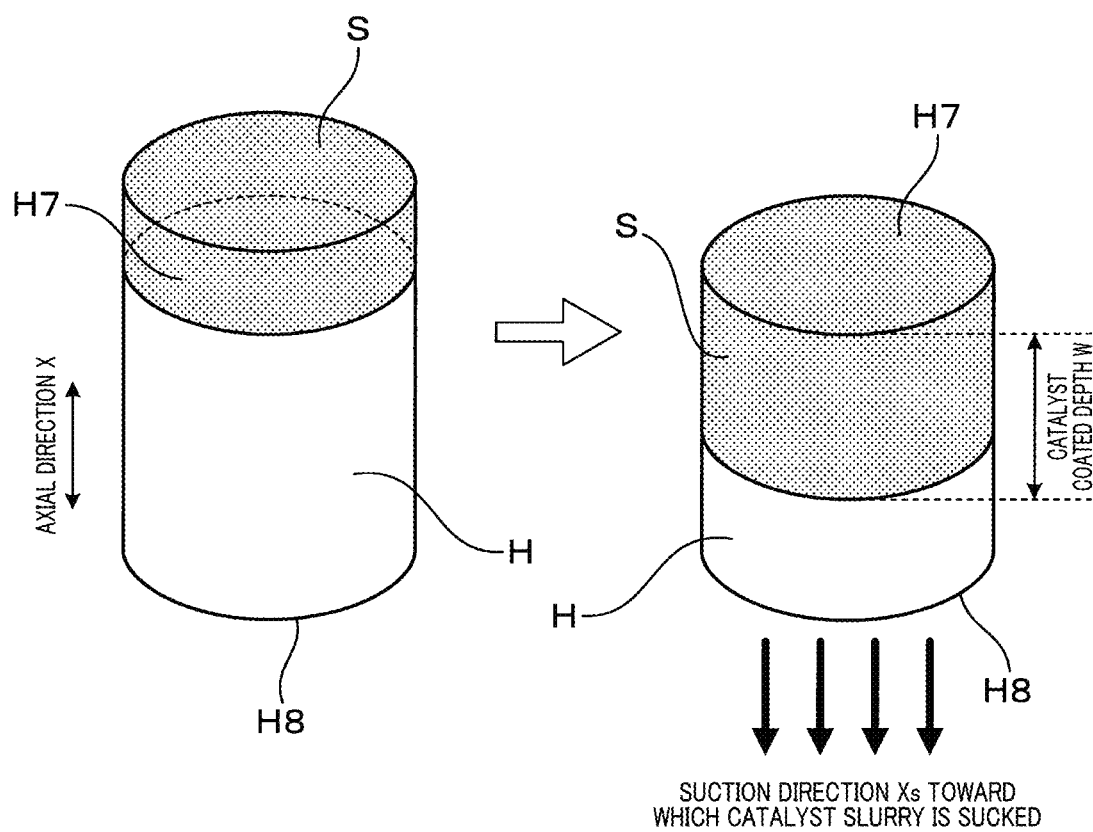
FIG. 13 is a schematic view explaining a catalyst slurry suction process in the manufacturing method according to the second exemplary embodiment, by which a catalyst slurry is sucked toward the suction direction Xs in the inside of the honeycomb structural body, and supported on the cell walls in the honeycomb structural body.

FIG. 13 is a schematic view explaining a catalyst slurry suction process in the manufacturing method according to the second exemplary embodiment. The catalyst slurry suction process sucks a catalyst slurry S toward a suction direction Xs into the inside of the honeycomb structural body as the test sample. The inside of the cells, i.e. the surface of the cell walls are coated with the catalyst by the catalyst slurry suction process.

As shown in FIG. 13, the honeycomb structural body H has a first end surface H7 and a second end surface H8, and the first end surface H7 is formed opposite to the second end surface H8 in the honeycomb structural body H.

As shown in FIG. 13, in the catalyst slurry suction process, the catalyst slurry S was prepared in contact with the first end surface H7 in the axial direction X of the honeycomb structural body H. Next, the catalyst slurry S was sucked toward the suction direction Xs which is equal to the axial direction X of the honeycomb structural body H. The surface of the cell walls were coated with the sucked catalyst slurry S.

In general, the manufacturing method according to the second exemplary embodiment further performs the catalyst slurry suction process from the second end surface H8 of the honeycomb structural body H. However, the catalyst coating test performed the catalyst slurry suction process only from the first end surface H7, and did not perform the catalyst slurry suction process from the second surface H8 of the honeycomb structural body H.

This makes it possible to correctly and clearly detect suction variation of the catalyst slurry S, i.e. variation of a catalyst coated depth W measured from the first end surface H7 of the honeycomb structural body H.

It is possible to easily and correctly detect the presence of the coated area, which is coated with the catalyst slurry S, on the basis of graduations of color because the coated area of the catalyst slurry S has a dark color. It is accordingly possible to detect the catalyst coated depth W of the catalyst slurry S measured from the first end surface H7 of the honeycomb structural body H as a test sample.

FIG. 12(a) to FIG. 12(d) are photographs showing a difference d of variation of the catalyst coated depth W measured from the first end surface H7 in the suction direction Xs of each of the honeycomb structural bodies as the test samples produced by the manufacturing method according to the second exemplary embodiment. In particular, FIG. 12(a) is a photograph showing the difference d of variation of the catalyst coated depth W measured from the first end surface H7 in the suction direction Xs of the honeycomb structural body H made from the clay rod produced by performing the mixing process once. FIG. 12(b) shows a photograph showing the difference d of variation of the catalyst coated depth W measured from the first end surface H7 in the suction direction Xs of the honeycomb structural body H made from the clay rod produced by performing the mixing process twice. FIG. 12(c) shows a photograph showing the difference d of variation of the catalyst coated depth W measured from the first end surface H7 in the suction direction Xs of the honeycomb structural body H made from the clay rod produced by performing the mixing process three times. FIG. 12(d) shows a photograph showing the difference d of variation of the catalyst coated depth W measured from the first end surface H7 in the suction direction Xs of the honeycomb structural body H made from the clay rod produced by performing the mixing process once with 10% increased reduction rate R.

As shown in FIG. 12(a) to FIG. 12(d), it is possible to calculate the difference d by subtracting the maximum catalyst coated depth from the maximum catalyst coated depth, measured from the first end surface H7 of each test sample. The variation of the catalyst coated depth W is often generated at a boundary between a deformation area in which waved cell walls are generated and a normal area in which no waved cell wall is generated. Accordingly, after a catalyst coating process, the test sample as the honeycomb structural body H is cut in a direction parallel to the axial direction X, and the cut surface is photographed. FIG. 12(a) to FIG. 12(d) show the photographs of the cut surfaces of the test samples. In general, the catalyst coated area coated by the catalyst slurry has a dark color when compared with a color of the non-coated area. It is possible to detect the difference d on the basis of the light and shade pattern.

The second exemplary embodiment used, as a catalyst slurry having thixotropy property, a slurry composed of a solid component at 70 wt %, and a binder at 1.4 wt % and water as a remainder. The solid component is a mixture of alumina, ceria zirconia, barium sulfate, etc.

As shown in FIG. 7(a) to FIG. 7(d), it is clearly understood that the more the number of times of performing the mixing process increases, the lighter the dark color derived from the lamination of the abnormality part 25. Further, it is clearly understood that the higher the reduction rate R is, the lighter the dark color derived from the lamination of the abnormality part 25.

Further, as shown in FIG. 8, FIG. 9 and Table 1, the more the number of times of performing the mixing process increases, the more the difference $\Delta T1$ and the difference $\Delta T2$ is reduced. That is, the difference $\Delta T1(\%)$ is a difference between the T1 relaxation time $N_{T1}$ (ms) of the normal part 24 and the T1 relaxation time $A_{T1}$ (ms) of the abnormality part 25, and the difference $\Delta T2(\%)$ is a difference between the T2 relaxation time $N_{T2}$ (ms) of the normal part 24 and the T2 relaxation time $\Delta T2$ (ms) of the abnormality part 25.

As shown in FIG. 10(a) to FIG. 10(d), it can be understood that the more the number of times of performing the mixing process increases and the higher the reduction rate R is, the lighter the dark color derived from the waved cell walls in the deformation area generated in the honeycomb structural body as a test sample.

Further, as shown in FIG. 11(a) to FIG. 11(d), it can be understood that the more the difference $\Delta T1$ and the difference $\Delta T2$ is reduced, the more the area of the waved cell walls is reduced.

Still further, as shown in FIG. 12(a) to FIG. 12(d), it can be understood that when the difference $\Delta T1$ and the difference $\Delta T2$ is more reduced, the difference d of variation of the catalyst coated depth W measured from the first end surface H7 in the suction direction Xs of the honeycomb structural body H is more reduced.

That is, it is possible to determine, i.e. to adjust the mixing condition of the raw materials in the mixing machine 4 and to adjust the compression condition of compressing a clay in the extrusion process by the screw extruder machine 3 of the mixing and screw extruder machine M on the basis of at least one of the calculated differences $\Delta T1$ and $\Delta T2$.

Further, it is preferable to perform the mixing process and the extrusion process on the basis of the mixing condition of the raw materials and the compression condition so that at least one of the calculated differences $\Delta T1$ and $\Delta T2$ is within a predetermined range. The mixing condition in the mixing process corresponds to the number of times of performing the mixing process, and the compression condition in the extrusion process corresponds to the reduction rate R.

As can be understood from the experimental results, i.e. from the photographs shown in FIG. 12(a) to FIG. 12(d), the difference d of variation of the catalyst coated depth W measured from the first end surface H7 in the suction direction Xs of a test sample (as the honeycomb structural body) almost does not almost vary if the number of times of performing the mixing process (i.e. the mixing condition in the mixing process) becomes not less than two times. That is, the difference d indicating the variation of the catalyst coated depth W has a small value, i.e. the catalyst coated depth W does not almost vary when the difference $\Delta T1$ is not more than 2.3% and the difference $\Delta T2$ is not more than 1.3%.

In view of the influence from variation of manufacturing equipment and properties of pores in the cell walls, it is possible to neglect the differences d of variation of the catalyst coated depth W as long as the difference $\Delta T1$ is not more than 2.3% and the difference $\Delta T2$ is not more than 1.3%.

It can be understood to adequately suppress the generation of waved cell walls and to reduce the difference d of variation of the catalyst coated depth W in the honeycomb structural body by repeatedly performing the mixing process or by compressing the clay in the extrusion process until the difference $\Delta T1$ becomes not more than 2.3% and/or the difference $\Delta T2$ becomes not more than 1.3%.

It is acceptable to adjust at least one of or both the mixing condition in the mixing process and the compression condition in the extrusion process as long as the difference $\Delta T1$ is set to a value of not more than 2.3% and/or the difference $\Delta T2$ is set to a value of not more than 1.3%.

Still further, it is acceptable to determine the mixing condition in the mixing process and the compression condition in the extrusion process so as to satisfy at least one of the difference $\Delta T1$ of not more than 2.3% and the difference $\Delta T2$ of not more than 1.3%. It is further acceptable to adjust the mixing condition in the mixing process and the compression condition in the extrusion process so as to satisfy both the difference $\Delta T1$ of not more than 2.3% and the difference $\Delta T2$ of not more than 1.3%.

It is more preferable for the manufacturing method according to the second exemplary embodiment to perform each of the mixing process and the extrusion process under the mixing condition and the compression condition so that the difference $\Delta T1$ becomes not more than 1.3% or until the difference $\Delta T2$ becomes not more than 1.1%. This case makes it possible to further suppress generation of defects such as waved cell walls in the honeycomb structural body.

As previously described in detail, the manufacturing method according to the second exemplary embodiment produces the extrusion molded body 2 (i.e. the clay rod 21)

and the honeycomb molded body 22 having less number of defects such as waved cell walls. It is therefore possible for the manufacturing method according to the second exemplary embodiment to produce the honeycomb structural body H having less number of defects by using the extrusion molded body 2 (clay rod 21).

The concept of the present invention is not limited by the first exemplary embodiment and the second exemplary embodiment previously described. It is possible for the present invention to provide various modifications within the scope of the present invention. For example, it is acceptable to perform the mixing process on the basis of a temperature of cooling water which flows in the mixing machine 4 in the mixing and screw extruder machine M and/or a chemical composition of constituent components, i.e. ceramic raw material, binder, lubricant, water, etc., in addition to the mixing condition (the number of times of performing the mixing process). That is, it is possible to reduce the difference ΔT1 and the difference ΔT2 by increasing the number of times of performing the mixing process, by reducing a temperature of the cooling water and/or by reducing an amount of water in the constituent components. This means that because a shearing stress increases when a viscosity of the clay 1 increases, it is possible to perform the mixing process within a short period of time.

There are, as the compression condition of the extrusion process, a length of the resistant tube 35, a temperature of cooling water flowing in the screw extruder machine 3 in addition to the reduction rate R of the resistant tube 35.

It is possible to reduce the difference ΔT1 and the difference ΔT2 by increasing the reduction rate R of the resistant tube 35, by using the resistant tube 35 having a long length, and by reducing the temperature of the cooling water flowing in the screw extruder machine 3. This means that those conditions break liquid films which cover the clay 1 which has been supplied from the mixing machine 4, and is mixed and extruded by the screw extruder machine 3.

While specific embodiments of the present invention have been described in detail, it will be appreciated by those skilled in the art that various modifications and alternatives to those details could be developed in light of the overall teachings of the disclosure. Accordingly, the particular arrangements disclosed are meant to be illustrative only and not limited to the scope of the present invention which is to be given the full breadth of the following claims and all equivalents thereof.

What is claimed is:

1. An evaluation method of evaluating properties of an extrusion molded body made from a clay to be used for producing a honeycomb structural body, where the extrusion molded body is produced by mixing constituent components which contain at least ceramic raw material, binder, lubricant and water to produce a clay and by extruding the clay through a screw extruder machine, and by compressing the extruded clay through a resistant tube in the screw extruder machine to produce the extrusion molded body, wherein the evaluation method comprises processes of:

performing a pulse Nuclear Magnetic Resonance to detect at least one of a T1 relaxation time of nuclear spins of water protons magnetically excited for each of a normal part and an abnormality part in the extrusion molded body and a T2 relaxation time of nuclear spins of water protons magnetically excited for each of the normal part and the abnormality part in the extrusion molded body, the normal part being a part where the water is retained with the extrusion molded body, and the abnormality part being a part where the water is seeped on a surface of the extrusion molded body; and performing evaluation of a uniformity of a mixed state and a compression state of the extrusion molded body on a basis of at least one of a difference in the T1 relaxation time between the normal part and the abnormality part, and a difference in the T2 relaxation time between the normal part and the abnormality part.

2. The evaluation method of evaluating properties of an extrusion molded body according to claim 1, wherein the evaluation method uses a clay rod as the extrusion molded body.

3. The evaluation method of evaluating properties of an extrusion molded body according to claim 1, wherein the abnormality part in the extrusion molded body is a lamination part from which water has been separated, and the normal part is a non-lamination part with water.

4. The evaluation method of evaluating properties of an extrusion molded body according to claim 1, wherein the extrusion molded body is a honeycomb molded body.

5. The evaluation method of evaluating properties of an extrusion molded body according to claim 4, wherein the abnormality part is a waved cell wall generated in the honeycomb molded body, and the normal part is a non-waved cell wall formed in the honeycomb molded body.

6. A manufacturing method of producing an extrusion molded body to be used for manufacturing a honeycomb structural body, the manufacturing method comprising processes of:

mixing constituent components which contain at least ceramic raw material, binder, lubricant and water to produce a clay;

extruding the clay by a screw extruder machine and compressing the extruded clay through a resistant tube in the screw extruder machine to produce the extrusion molded body;

performing a pulse Nuclear Magnetic Resonance to detect at least one of a T1 relaxation time of nuclear spins of water protons magnetically excited for each of a normal part and an abnormality part in the extrusion molded body and a T2 relaxation time of nuclear spins of water protons magnetically excited for each of the normal part and the abnormality part in the extrusion molded body, the normal part being a part where the water is retained with the extrusion molded body, and the abnormality part being a part where the water is seeped on a surface of the extrusion molded body, and performing an evaluation of uniformity of a mixed state and a compression state of the extrusion molded body on a basis of at least one of a difference in the T1 relaxation time between the normal part and the abnormality part, and a difference in the T2 relaxation time between the normal part and the abnormality part; and determining a mixing condition in the mixing process and a compression condition in the extrusion process on the basis of at least one of the difference in the T1 relaxation time between the normal part and the abnormality part, and the difference in the T2 relaxation time between the normal part and the abnormality part.

7. The manufacturing method of producing an extrusion molded body according to claim 6, wherein the manufacturing method performs the mixing process and the extrusion process on the basis of the mixing condition so that at least one of the difference of the T1 relaxation time and the difference of the T2 relaxation time becomes within a predetermined range.

8. The manufacturing method of producing an extrusion molded body according to claim 6, wherein the manufacturing method performs the mixing process and the extrusion process on the basis of the mixing condition so that the difference of the T1 relaxation time becomes not more than 2.3% or the difference of the T2 relaxation time becomes not more than 1.3%.

9. The manufacturing method of producing an extrusion molded body according to claim 6, wherein the manufacturing method performs the mixing process and the extrusion process on the basis of the mixing condition so that the difference of the T1 relaxation time becomes not more than 1.3% or the difference of the T2 relaxation time becomes not more than 1.1%.

10. The manufacturing method of producing an extrusion molded body according to claim 6, wherein the manufacturing method uses a clay rod as the extrusion molded body.

11. The manufacturing method of producing an extrusion molded body according to claim 6, wherein the abnormality part in the extrusion molded body is a lamination part from which water has been separated, and the normal part is a non-lamination part with water.

12. The manufacturing method of producing an extrusion molded body according to claim 6, wherein the extrusion molded body is a honeycomb molded body.

13. The manufacturing method of producing an extrusion molded body according to claim 12, wherein the abnormality part is a waved cell wall generated in the honeycomb molded body, and the normal part is a non-waved cell wall formed in the honeycomb molded body.

* * * * *